United States Patent [19]

Kira et al.

[11] Patent Number: 5,365,563
[45] Date of Patent: Nov. 15, 1994

[54] FLUORESCENT X-RAY QUANTITATIVE ANALYSIS APPARATUS

[75] Inventors: Akimichi Kira; Haruto Sugishita, both of Miyanohigashi, Japan

[73] Assignee: Horiba, Ltd., Kyoto, Japan

[21] Appl. No.: 23,047

[22] Filed: Feb. 25, 1993

[30] Foreign Application Priority Data

Feb. 29, 1992 [JP] Japan .................. 4-079240

[51] Int. Cl.⁵ .......................................... G01N 23/20
[52] U.S. Cl. ............................ 378/48; 378/44; 378/45
[58] Field of Search ............ 378/44, 45, 46, 47, 378/48, 50, 111, 109, 114, 115, 156, 157, 158, 159

[56] References Cited

U.S. PATENT DOCUMENTS

| | | | |
|---|---|---|---|
| 3,701,899 | 10/1972 | Voparil | 378/45 |
| 3,919,548 | 11/1975 | Porter | 378/45 |
| 4,015,124 | 3/1977 | Page | 378/45 |
| 4,260,885 | 4/1981 | Albert | 378/45 |
| 5,179,580 | 1/1993 | Komatani et al. | |

Primary Examiner—David P. Porta
Attorney, Agent, or Firm—Price, Gess & Ubell

[57] ABSTRACT

A fluorescent X-ray quantitative analysis apparatus generates a stream of primary X-rays that are subject to variable conditions such as voltage, X-ray filters, and gas conduit conditions. A sample is supported to receive the beam of primary X-rays, and then measurements are made of the secondary X-rays resulting from impact with the sample. Conditions are changed to affect the primary X-rays, and a second measurement is made of the secondary X-rays from the sample. A computer circuit can determine the concentration of elements in the sample from their respective measurements, for example, by resolving a plurality of simultaneous equations.

10 Claims, 5 Drawing Sheets

FLUORESCENT X-RAY QUANTITATIVE ANALYSIS APPARATUS

BACKGROUND OF THE INVENTION

1. Field of the Invention

The present invention relates to a fluorescent x-ray quantitative analysis apparatus in which primary X-rays can be applied to a sample to enable a quantitative analysis of the sample on the basis of secondary X-rays emitted from the sample and, more particularly, to vary the conditions in which readings are taken, and determining the concentrations of elements based on a plurality of readings.

2. Description of Related Art

Elements in a sample have been quantitatively determined by the use of an energy dispersive X-ray fluorescent analyzer in the prior art. The fluorescent X-rays of elements heavier than Na (sodium) can usually be measured at the same time. The intensities of these fluorescent X-rays are proportional to concentrations of the respective elements in a first approximation, but the results can be greatly influence by coexisting elements in the sample due to absorption and secondary excitation effects.

As a result, the intensities of the respective fluorescent X-rays are expressed by a function of the concentrations of all the elements that are existing in a sample that is measured. This function can be theoretically calculated, and a comparison with an actual measured intensity can be conducted over a number of times equal to the number of elements in the sample. This method, in which a plurality of comparison equations or expressions are solved, as simultaneous equations, is called the fundamental parameter method.

In a conventional fluorescent X-ray quantitative determination, measurement conditions are set, such as the magnitude of a voltage (X-ray tube voltage), which is applied between a filament and a target in an X-ray tube, the particular material of a primary X-ray filter and a particular thickness is determined, and whether the X-ray beam will pass through a vacuum or air, is set. The sample is then measured under these fixed conditions, and the simultaneous equations are then set up on the basis of the intensities of the fluorescent X-rays obtained at that time. The simultaneous equations are then resolved by the use of, for example, the fundamental parameter method, to determine the concentrations of elements contained in the sample, as shown in FIG. 4. FIG. 4 sets forth the process steps in such a conventional method.

A disadvantage, however, has occurred if the measuring conditions that are set for the measurement of light elements are utilized for a sample containing elements having separate atomic numbers in mixture, since the sensitivity for heavy elements is substantially lowered. Conversely, if the measurement conditions are set to be suitable for the measurement of heavy elements, then the sensitivity for light elements is lowered, and the accuracy of the measurement will deteriorate.

As can be appreciated, this field is still looking for an optimum method of measuring multiple elements in a sample.

SUMMARY OF THE INVENTION

An improved fluorescent X-ray quantitative analysis apparatus is provided wherein a beam of primary X-rays can be relatively varied through the setting of different conditions, such as a variable voltage source to the X-ray tube, the selection of one of a number of variable primary X-ray filters, and controlling the environment in which the X-ray beam passes to the sample, such as in air, vacuum, nitrogen, etc. A sample is supported to receive the beam of primary X-rays after they have left the X-ray tube and have passed through the primary X-ray filter. The primary X-rays impact the sample and produce secondary X-rays, such as fluorescent X-rays and scattered X-rays. These secondary X-rays are characteristic of elements contained in the sample. The X-rays from the sample at a predetermined condition can be measured, and then the conditions can be altered with a second measurement of the X-rays being conducted, to provide a new set of measurements. The number of measurements can be repeated as desired to provide sufficient information for determining the concentrations of elements in the sample from each of the respective measurements. The conditions can be altered by changing one or more of the voltage to the X-tube, the particular primary X-ray filter and its thickness, and varying the gas or the lack of gas contained in a conduit, which delivers the primary X-rays to the sample. A computer circuit can be used for resolving a plurality of simultaneous equations based on each of the respective measurements to provide an accurate determination of both light elements and heavy elements contained in the same sample.

It is an object of the present invention to provide a fluorescent X-ray quantitative analysis capable of quantitatively determining both light elements and heavy elements with high accuracy, even in a case where elements having separate atomic numbers are contained within the same sample. The data received from multiple measurements based upon varying measuring conditions enables simultaneous equations to be established based on the measured data, and then resolved by, for example, the fundamental parameter method or the calibration curve method, to determine the specific concentrations of the elements contained in the sample.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved fluorescent X-ray quantitative analysis apparatus that can be used on samples with a plurality of components therein.

Figure 2:
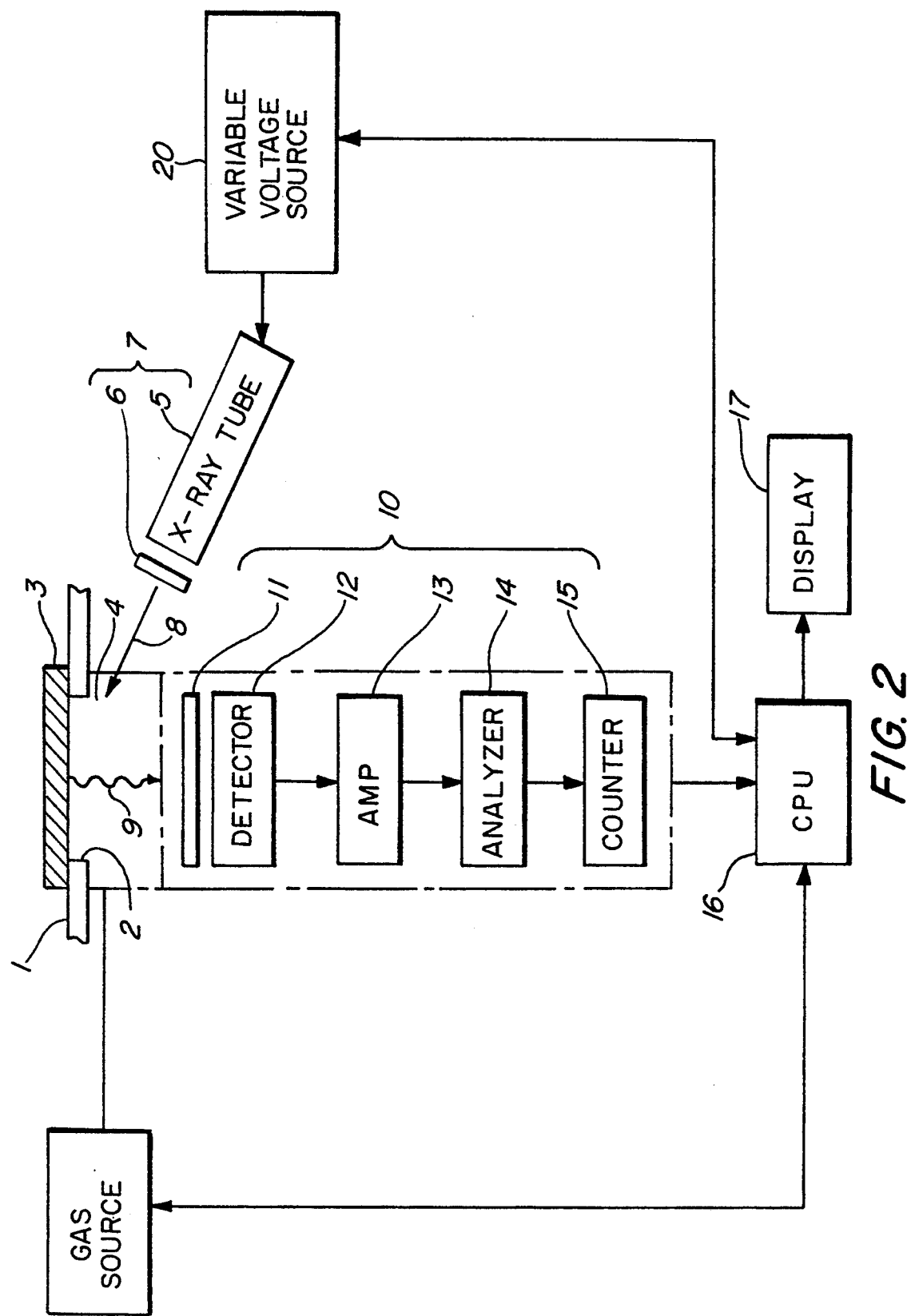
FIG. 2 is a drawing disclosing a schematic form of one example of the fluorescent X-ray analyzer of the present invention.

Referring to FIG. 2, a schematic diagram of the present invention is disclosed in the form of a fluorescent X-ray analyzer. A sample supporting table 1 provided with an opening 2 is constructed to support a sample in an operative position to receive the sample 3. An X-ray source 7 can comprise an X-ray tube 5 and can include a replaceable primary X-ray filter 6 in a position to communicate with the chamber beneath the table 1. A variable voltage source 20 can be utilized to vary the quantity of X-rays produced by the X-ray source 7. Additionally, the X-ray filter 6 can be exchanged to also vary the quantity of X-rays that will be available to impact the sample 3. The enclosed chamber beneath the sample table 1 and the sample 3 can have control conditions so that it can be evacuated or it can receive gas, such as nitrogen or air, for example, from a gas source 22. The presence or absence of gas and the particular gas within the chamber can also determine the quantity of X-rays impacting the sample 3. The varying of the gaseous condition, e.g., type of gas and pressure, or absence of gas, e.g., vacuum, can be automatically controlled by a computer in coordination with the measurement of secondary X-rays from the sample.

The X-ray tube 5 comprises, for example, an electron gun emitting electron beams and a target turning the emitted electron beams into predetermined primary X-rays and reflecting these primary X-rays in the direction of the sample target 3. The primary X-rays pass from the X-ray tube 5 through the primary X-ray filter 6 to be turned into primary X-rays 8 having an energy distribution highly efficient for exciting, for example, a certain element. This X-ray beam 8 is applied to the sample 3 through the X-ray passing portion 4 or chamber beneath the sample table 1. As a result of the impacting of these selected primary X-rays 8, secondary X-rays 9, including fluorescent X-rays, scattered X-rays, and the like, are emitted from the sample 3.

A secondary X-ray-detecting portion 10 is utilized to detect the secondary X-rays 9 which also pass through the X-ray passing portion or chamber 4. The secondary X-ray-detecting portion 10 comprises an X-ray filter 11 for absorbing background components in the vicinity of energies to be measured, a semiconductor detector 12, an amplifier 13, a pulse height analyzer 14, and a counter 15, in that order.

The intensities of the fluorescent X-rays and the scattered X-rays will correspond to a concentration of an element to be measured in the sample. This measured data can be stored and analyzed by a computer circuit CPU 16. Known software programs are capable of resolving the measured data and providing an output display, as shown as display 17 in FIG. 2. The computer circuits as shown in FIG. 2, can optionally monitor and control the various variable conditions that can influence each measurement, such as the voltage source 20 for the X-ray tube 5 and the gas source 22. The gas source 22 can include stored containers of gas, valves, pumps, and electromechanical controls that are responsive to both operator- and computer-generated control signals.

Figure 1:
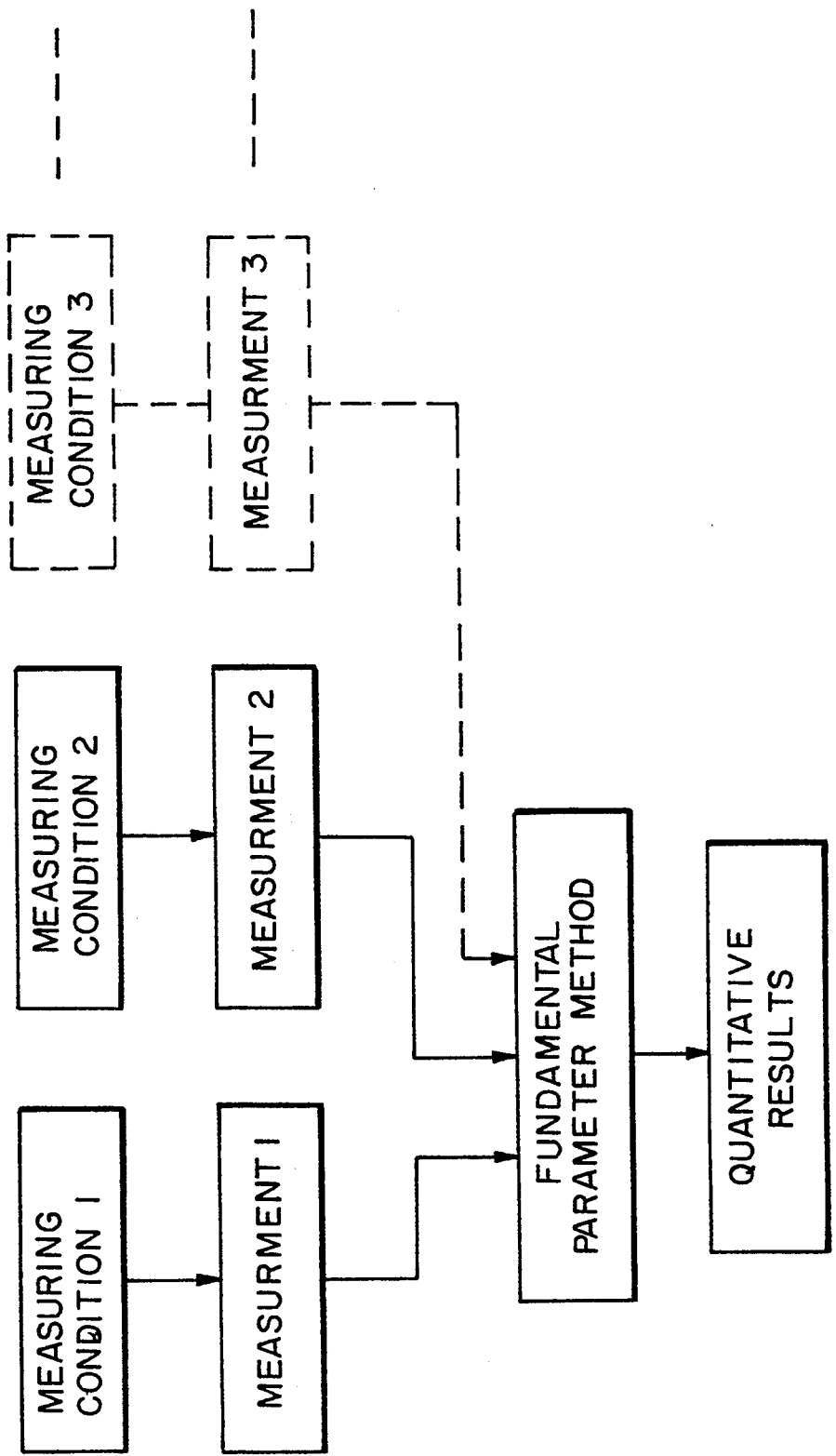
FIG. 1 is a diagram disclosing the procedures of the fluorescent X-ray quantitative analysis system according to the present invention.

Referring to FIG. 1, the system of determining a plurality of elements in the sample are shown. This is accomplished by taking a series of measurements 1. 2, 3, etc., with each measurement being taken with a varying of the measuring condition. Thus, in FIG. 1, measuring condition 1 is taken for measurement 1, while measuring condition 2 is used for measurement 2. The data produced from each of these of measurement cycles can be utilized to provide simultaneous equations which can be solved by a fundamental parameter method to determine the concentrations of the elements contained in the sample. The different measuring conditions by changing, for example, the magnitude of the tube voltage, the particular kind of the primary X-ray filter, or even the particular thickness of the filter, and gas or lack of gas conditions contained in the sealed chamber in which the selected primary X-rays 8 will pass on their way to the sample 3. Simultaneous equations that are produced under these different conditions can be established on the basis of the data obtained as a result of each of these measurements. The fundamental parameter method is a method of calculating the concentration of the elements from physical constants such as a mass absorption coefficient, the fluorescent yield, and transition probability.

Figure 3A:
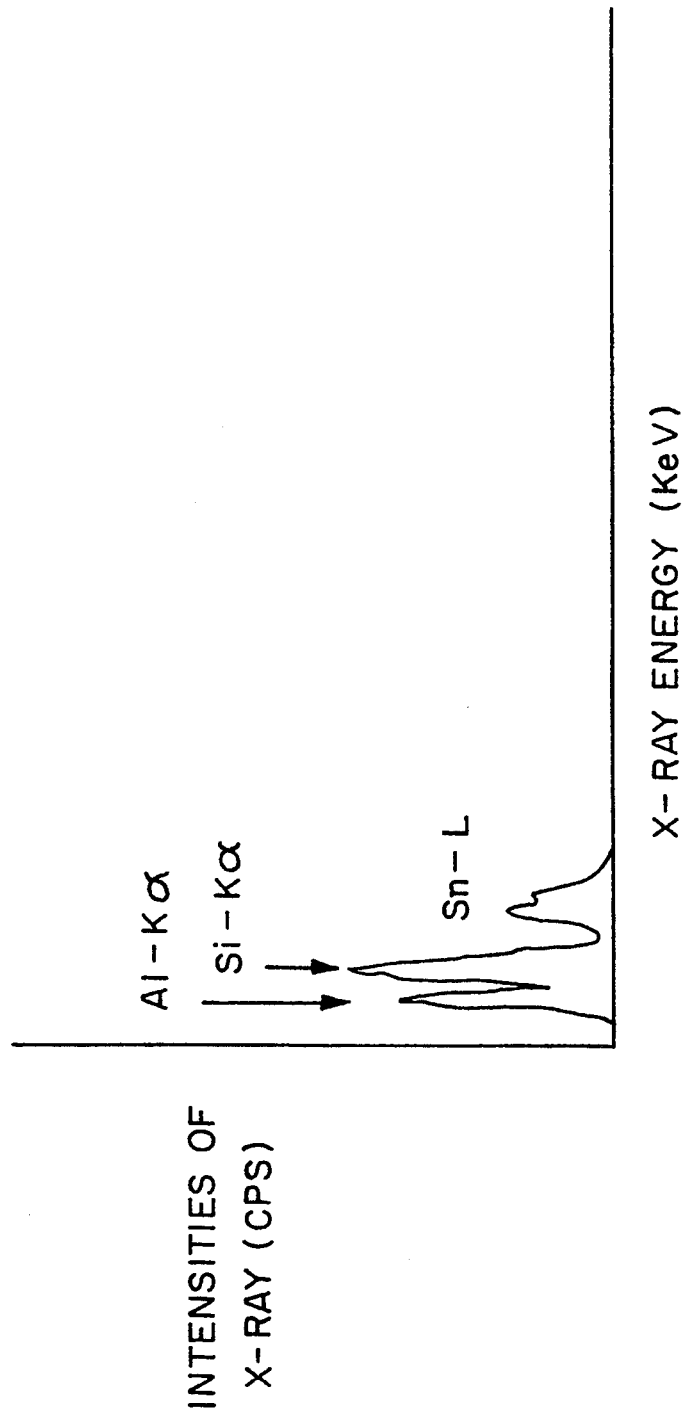
FIG. 3(A) is a drawing showing a spectrum of X-ray energy with a mixture comprising Al, Si, and Sn in a sample and a tube voltage of 15 KV.

The measurements are conducted by the use of a fluorescent X-ray analyzer having the above-described construction under the conditions that a mixture comprising Al (aluminum), Si (silicon), and Sn (tin) is used as the sample and the magnitude of voltage applied to the tube is different; that is, 15 KV and 50 KV, respectively. A spectrum obtained at this time is shown in FIG. 3(A) (the tube voltage of 15 (KV) and FIG. 3(b) (the tube voltage of 50 (KV), respectively.

The simultaneous equations for the fluorescent X-ray quantitative determination are expressed by the following Equation (1):

$$C_1 = \frac{I_i}{I_i^{pure}} \times \left( 1 = \sum_{\substack{i=1 \\ i \neq 1}}^{n} \alpha_{ij} \times C_j \right) \quad (1)$$

wherein i represents an element; $C_i$ represents a concentration of the i-element; $I_i$ represents an intensity of fluorescent X-rays resulting from the i-element contained in the sample; $I_i^{pure}$ represents an intensity of fluorescent X-rays resulting from the sample composed of merely the i-element; $\alpha_{ij}$ represents an influence coefficient of the j-element upon the i-element (a function of composition), and $C_j$ represents the concentration of the j-element.

As obvious from the above-described Equation (1), the accuracy of calculation for the concentration of each element is influenced by that of coexisting elements in the sample. Accordingly, in the case where the measurements are conducted at the tube voltage of 15 KV, a Sn-K line cannot be detected for a 10 sample containing light elements, such as Al and Si, and a heavy element, such as Sn, together, as shown in FIG. 3(A). In order to calculate the concentration of Sn, an Sn-L line is used, but the Sn-L line is inferior to an Sn-K line (refer to FIG. 3(B)) obtained at a tube voltage of 50 KV in sensitivity of detection. Thus, not only the concentration of Sn, but also the concentrations of other elements, will be deteriorated in the accuracy of calculation.

Figure 3B:
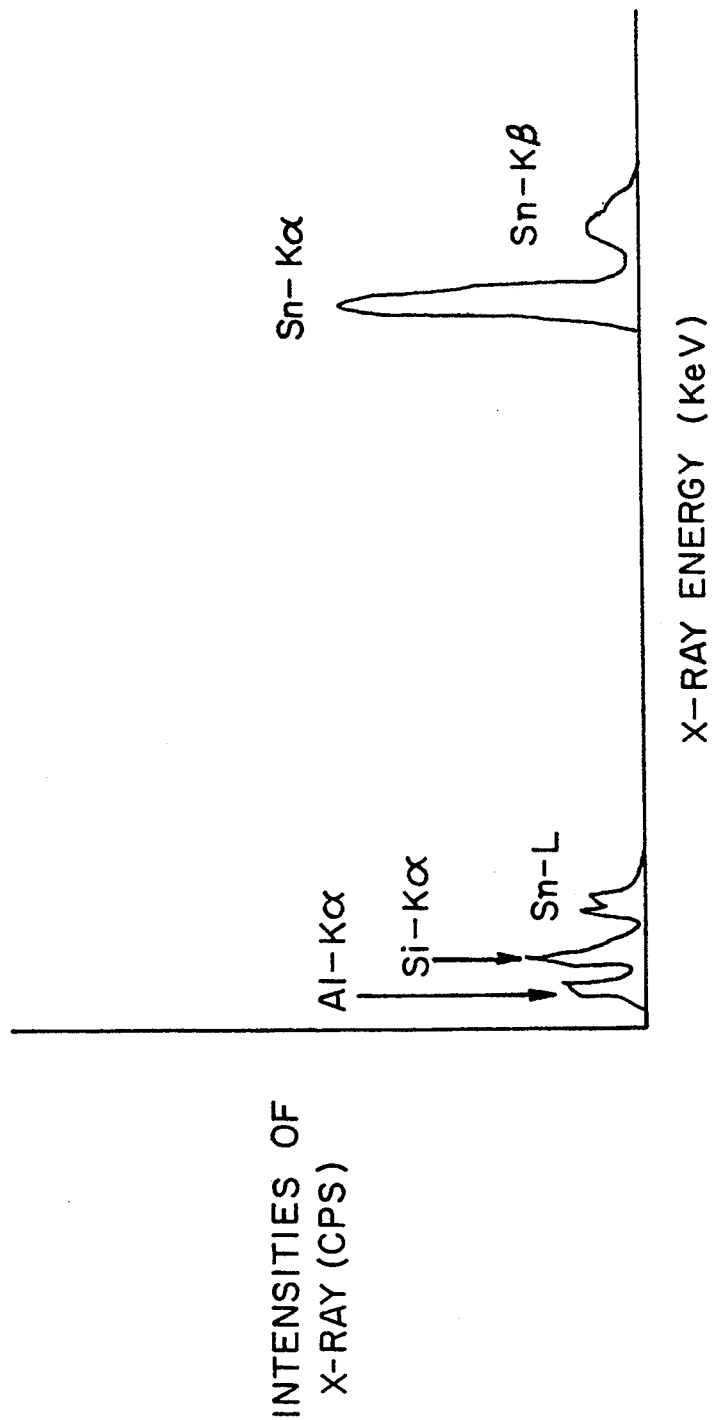
FIG. 3(B) is a drawing showing a spectrum of X-ray energy with the tube voltage varied to 50 KV.
Figure 4:
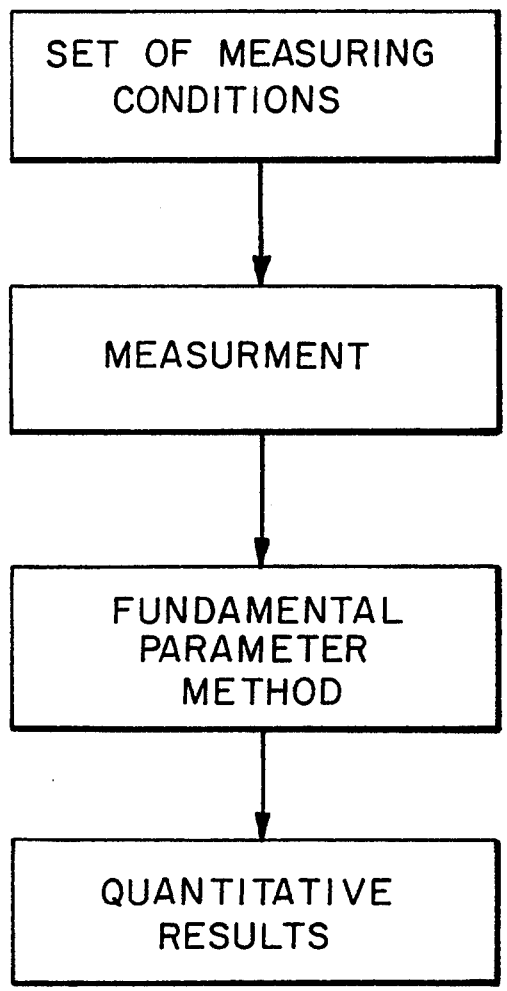
FIG. 4 is a diagram disclosing a conventional fluorescent X-ray quantitative analysis method.

In the case where the above-described sample is measured at the tube voltage of 50 KV, the intensity of the Sn-K line is increased, but the intensities of the Al-K line and the Si-K line are reduced, as shown in FIG. 3(B). Accordingly, the intensity of the Al-K line and the Si-K line, respectively, obtained when the measurement is conducted at the tube voltage of 15 KV is used for Al and Si, respectively. The intensity of the Sn-K line obtained when the measurement is conducted at the tube voltage of 50 KV is used for Sn to set up the simultaneous equations based on the different measuring conditions and the simultaneous equations are worked out by a convergent calculation by the use of the fundamental parameter method. Thus, the concentrations of all elements can be calculated with high accuracy.

In addition, when the above-described simultaneous equations are worked out, a double-regressive calibration curve method, in which the influence coefficient is calculated by the use of standard samples, may also be used in place of the fundamental parameter method. Furthermore, the sample to be measured in the method according to the present invention is not limited by a solid sample, but could also be a thin-film sample and a liquid sample.

As described above, according to the present invention, the accuracy of quantitative determination can be improved. Thus, all elements including the light elements and the heavy elements can be quantitatively determined with high accuracy even in the case where elements having separate atomic numbers are contained in the same sample.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved fluorescent X-ray quantitative analysis apparatus comprising:

means for generating a stream of primary X-rays including a variable voltage source and a variable primary X-ray filter; means for supporting a sample to receive the beam of primary X-rays after translating through the primary X-ray filter;

first means for measuring the X-rays from the sample at a first predetermined condition of voltage and filter values;

second means for measuring the X-rays from the sample at a second predetermined condition of voltage and filter values wherein at least one conditioned value is changed from the first condition;

means for storing the measurements of the first and second means; and computer means for determining the concentrations of elements in the sample from the respective measurements of the first and second means including providing a corresponding simultaneous equation for each respective measurement and calculating the concentrations by a convergent calculation pursuant to a fundamental parameter method.

2. The invention of claim 1, further including a conduit for passing X-rays and means for varying a gas within the conduit to vary the quantity of X-rays wherein the first predetermined condition includes a first condition of gas and the second predetermined condition can include a second condition of gas different than the first condition.

3. The invention of claim 1 wherein the means for determining includes a computer circuit.

4. The invention of claim 1 wherein each simultaneous equation is expressed by the following equation:

$$C_1 = \frac{I_i}{I_i^{pure}} \times \left( 1 = \sum_{i=1}^{n} \alpha_{ij} \times C_j \right)$$

wherein i represents an element; $C_i$ represents a concentration of the i-element; $I_i$ represents an intensity of fluorescent X-rays resulting from the i-element contained in the sample; $I_i^{pure}$ represents an intensity of fluorescent X-rays resulting from the sample composed of merely the i-element; $\alpha_{ij}$ represents an influence coefficient of the j-element upon the i-element (a function of composition), and $C_j$ represents the concentration of the j-element.

5. An improved fluorescent X-ray quantitative analysis apparatus comprising:

a source of primary X-rays for generating a beam of primary X-rays;

means for supporting a sample to receive the beam of primary X-rays;

an enclosed chamber for passing the beam of primary X-rays from the source to the sample;

means for introducing and purging gas from the enclosed chamber to vary the transmission characteristics of the chamber for the primary X-rays;

means for measuring secondary X-rays generated after the impact of the primary X-rays with the sample;

control means for controlling the means for introduction of a gas to provide a first transmission characteristic in the chamber and recording a first measurement of the secondary X-rays and to subsequently provide a second transmission characteristic in the chamber and recording a second measurement of the secondary X-rays; and means for determining the concentration of elements in the sample from both the first and second measurements.

6. The invention of claim 5 wherein the means for determining includes a computer circuit for resolving a plurality of simultaneous equations based on the first and second measurements.

7. An improved fluorescent X-ray quantitative analysis apparatus comprising:

a source of primary X-rays;

means for varying a beam of primary X-rays from at least a first quantity to a second different quantity;

means for supporting a sample to receive the beam of X-rays;

means for measuring fluorescent X-rays resulting from the impacting of the sample by the first quantity of primary X-rays to provide a first measurement and by the second quantity of primary X-rays to provide a second different measurement; and computer means for providing a corresponding simultaneous equation representative of respectively the first measurement and the second measurement having the following equation:

$$C_1 = \frac{I_i}{I_i^{pure}} \times \left(1 = \sum_{i=1}^{n} a_{ij} \times C_j\right)$$

wherein i represents an element; $C_i$ represents a concentration of the i-element; $I_i$ represents an intensity of fluorescent X-rays resulting from the i-element contained in the sample; $I_i^{pure}$ represents an intensity of fluorescent X-rays resulting from the sample composed of merely the i-element; $a_{ij}$ represents an influence coefficient of the j-element upon the i-element (a function of composition), and $C_j$ represents the concentration of the j-element, the computer means automatically solving the simultaneous equations to calculate concentrations of elements by a convergent calculation pursuant to a fundamental parameter method.

8. The invention of claim 7 wherein the means for varying includes one of variable voltage sources applied to the source of primary X-rays, a variable filter and a variable gas condition for the transmission of the X-ray beams.

9. A method of determining the concentration of elements in a sample by fluorescent X-ray quantitative analysis comprising the steps of:
providing a source of primary X-rays;
placing a sample in a path to receive the primary X-rays;
varying a beam of primary X-rays from at least a first quantity to a second different quantity;
measuring the fluorescent X-rays emitted from the sample at the first quantity of primary X-rays;
measuring the fluorescent X-rays emitted from the sample at the second quantity of primary X-rays;
generating a corresponding simultaneous equation representative of respectively the measurement of the first and second quantity of primary X-rays having the following equation:

$$C_1 = \frac{I_i}{I_i^{pure}} \times \left(1 = \sum_{i=1}^{n} a_{ij} \times C_j\right)$$

wherein i represents an element; $C_i$ represents a concentration of the i-element; $I_i$ represents an intensity of fluorescent X-rays resulting from the i-element contained in the sample; $I_i^{pure}$ represents an intensity of fluorescent X-rays resulting from the sample composed of merely the i-element; $a_{ij}$ represents an influence coefficient of the j-element upon the i-element (a function of composition), and $C_j$ represents the concentration of the j-element; and
solving the simultaneous equations to determine the concentration of elements in the sample.

10. The method of claim 9 wherein the variations of the beaming of primary X-rays is accomplished by changing a gas through which the primary X-rays transit between the source and the sample.

* * * * *